United States Patent [19]

Wilk

[11] Patent Number: 5,269,772
[45] Date of Patent: Dec. 14, 1993

[54] LAPAROSCOPIC CANNULA ASSEMBLY AND ASSOCIATED METHOD

[76] Inventor: Peter J. Wilk, 185 W. End Ave., New York, N.Y. 10023

[21] Appl. No.: 913,469

[22] Filed: Jul. 14, 1992

Related U.S. Application Data

[63] Continuation-in-part of Ser. No. 825,158, Jan. 24, 1992, Pat. No. 5,183,471.

[51] Int. Cl.$^5$ ............................................. A61M 25/00
[52] U.S. Cl. ..................................... 604/284; 604/264
[58] Field of Search .............................. 604/280–284, 604/264; 128/4, 5; 285/136, 137.1

[56] References Cited

U.S. PATENT DOCUMENTS

| 1,266,552 | 5/1918 | Chapman | 285/137.1 |
| 1,519,018 | 12/1924 | Boudreau | 285/137.1 |
| 2,510,125 | 6/1950 | Meakin | 285/137.1 |
| 2,976,888 | 3/1961 | Merriman | 285/137.1 |
| 3,583,710 | 6/1971 | Burelle | 285/137.1 |
| 3,654,965 | 4/1972 | Gramain | 285/137.1 |
| 3,960,143 | 6/1976 | Terada | |
| 4,653,476 | 3/1987 | Bonnet | |
| 4,654,030 | 3/1987 | Moll et al. | 604/165 |
| 4,683,879 | 8/1987 | Williams | |
| 4,700,694 | 10/1987 | Shishedo | |
| 5,025,778 | 6/1991 | Silverstein et al. | |
| 5,099,827 | 3/1992 | Melzer et al. | |

*Primary Examiner*—C. Fred Rosenbaum
*Assistant Examiner*—Manuel Mendez
*Attorney, Agent, or Firm*—R. Neil Sudol; Henry D. Coleman

[57] ABSTRACT

A cannula assembly for use in laparoscopic surgery comprises a rigid tubular member and a first component connected to the tubular member and rigid therewith for defining, for a first laparoscopic instrument having a rigid shaft, a first insertion path through the tubular member and through a pre-established instrument-crossing region of predetermined area to be lodged in a patient's abdomen. A second component is connected to the tubular member and is at least partially separate from the first component for defining, for a second laparoscopic instrument having a rigid shaft, a second insertion path through the instrument-crossing region.

22 Claims, 2 Drawing Sheets

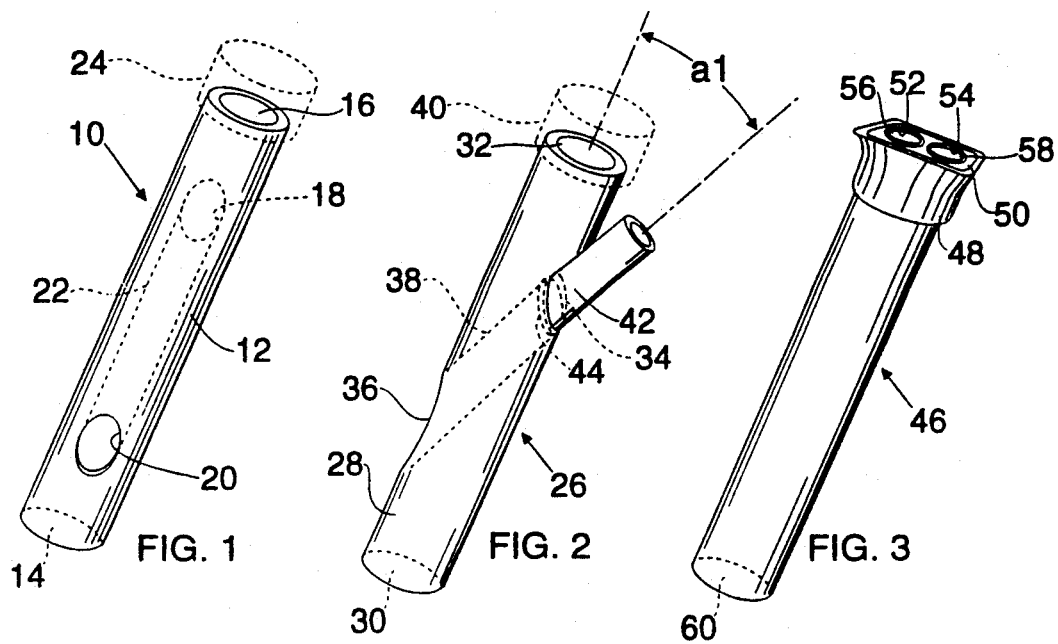
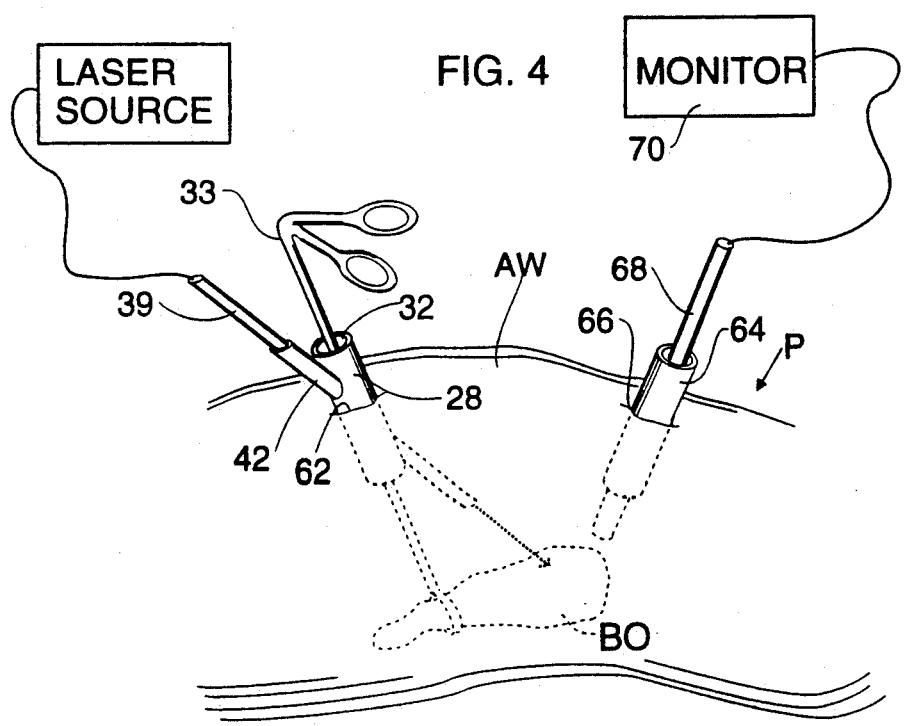

LAPAROSCOPIC CANNULA ASSEMBLY AND ASSOCIATED METHOD

CROSS-REFERENCE TO RELATED APPLICATION

This application is a continuation-in-part of application Ser. No. 825,158 filed Jan. 24, 1992, now U.S. Pat. No. 5,183,471.

BACKGROUND OF THE INVENTION

This invention relates to a laparoscopic cannula assembly or a trocar sleeve assembly. This invention also relates to a laparoscopic surgical technique involving such a cannula assembly.

Laparoscopy involves the piercing of a patient's abdominal wall and the insertion of a cannula through the perforation. Generally, the cannula is a trocar sleeve which surrounds a trocar during an abdomen piercing operation. Upon the formation of the abdominal perforation, the trocar is withdrawn while the sleeve remains traversing the abdominal wall. A laparoscopic instrument, such as a laparoscope or a forceps, is inserted through the cannula so that a distal end of the instrument projects into the abdominal cavity.

Generally, in a laparoscopic surgical procedure, three or four perforations are formed in the abdomen to enable deployment of a sufficient number of laparoscopic instruments to perform the particular surgery being undertaken. Each perforation is formed by a trocar which is surrounded by a sleeve, the sleeves or cannulas all remaining in the abdominal wall during the surgical procedure.

Prior to insertion of the first trocar and its sleeve, a hollow needle is inserted through the abdominal wall to enable pressurization of the abdominal cavity with carbon dioxide. This insufflation procedure distends the abdominal wall, thereby producing a safety space above the patient's abdominal organs.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

It frequently occurs during laparoscopic surgery that an additional instrument is temporarily required. Inserting this extra instrument involves either temporarily removing one of the other instruments or forming another perforation with a trocar.

OBJECTS OF THE INVENTION

An object of the present invention is to provide a device and an associated method for facilitating laparoscopic surgery.

A particular object of the present invention is to provide a trocar sleeve or laparoscopic cannula which facilitates the temporary insertion of an extra laparoscopic instrument during a laparoscopic procedure.

A further particular object of the present invention is to provide a method for the temporary insertion of an extra laparoscopic instrument during laparoscopic surgery which does not require the formation of another perforation in the abdominal wall or the removal of another instrument from the abdomen.

An even more particular object of the present invention is to provide a trocar sleeve or laparoscopic cannula which is easy to use and to manufacture.

SUMMARY OF THE INVENTION

A cannula assembly for use in laparoscopic surgery comprises, in accordance with the present invention as set forth in amended claim, a rigid tubular member and a first component connected to the tubular member and rigid therewith for defining, for a first laparoscopic instrument having a rigid shaft, a first insertion path through the tubular member and through a pre-established instrument-crossing region of predetermined area to be lodged in a patient's abdomen. A second component is connected to the tubular member and is at least partially separate from the first component for defining, for a second laparoscopic instrument having a rigid shaft, a second insertion path through the instrument-crossing region.

Pursuant to another feature of the present invention, the first component includes a port member attached to the tubular member at one end thereof, while the second component includes a rigid tube attached to the tubular member. In one particular embodiment of the invention, the tube is pivotably attached to the tubular member at or about the pre-established crossing region and is provided at one end with a port attachment movably connected to the port member on the tubular member. The port attachment may be slidably or, alternatively, pivotably connected to the port member.

In another particular embodiment of the present invention, the tube is rigidly attached to the tubular member. In addition, the tube is provided with a port member rigidly attached to the port member of the tubular member.

A cannula assembly for use in laparoscopic surgery comprises, in accordance with the present invention, a rigid first tubular member and a rigid second tubular member. The tubular members each have a proximal end, a distal end and a central region. The tubular members are connected to one another at the respective proximal ends and, optionally, at the central regions.

Pursuant to another feature of the present invention, the tubular members are connected to one another only at their central regions and their proximal ends. Pursuant to a more specific feature of the present invention, the central regions are movably connected to one another and the proximal ends are movably connected to one another. In a specific embodiment of the invention, the central region of the first tubular member is pivotably connected to the central region of the second tubular member, whereas the proximal end of the first tubular member is pivotably connected to the proximal end of the second tubular member. In an alternative specific embodiment of the invention, the central regions are pivotably connected to one another and the proximal ends are slidably connected to one another.

According to another feature of the present invention, the tubular members are rigidly connected to one another at the proximal ends. In that event, they may be rigidly connected only at their proximal ends, e.g., via an insufflation port member.

Pursuant to an additional feature of the present invention, the first tubular member is oriented at an angle with respect to the second tubular member. Where the tubular members are rigidly connected to one another, the relative angular disposition is permanent. In other cases, where the tubular members are movably, e.g., pivotably, connected to one another, the relative angular disposition occurs upon an adjustment of the cannular assembly from a tube parallel configuration to a tube angled configuration.

A laparoscopic cannula assembly comprises, in accordance with a particular embodiment of the present invention, a rigid tubular member and a cap attached to the tubular member at a proximal end thereof, the cap being provided with a pair of coplanar insertion ports in a transversely oriented wall of the end cap. A pair of insufflation stoppers are movably attached to the cap along an inner side of the wall and covering respective ones of the ports.

A method for use in laparoscopy comprises, in accordance with the present invention, the steps of (a) forming a perforation in a patient's abdominal wall, (b) disposing in the perforation a cannula assembly including at least one rigid tubular member, (c) inserting a distal end of a first laparoscopic instrument through the cannula assembly and into the patient's abdominal cavity, (d) inserting a distal end of a second laparoscopic instrument through the cannula assembly and into the patient's abdominal cavity while the first laparoscopic instrument is partially disposed in the cannula assembly, (e) manipulating the second laparoscopic instrument from outside the patient to perform a surgical operation inside the patient, and (f) withdrawing the second laparoscopic instrument from the patient's abdominal cavity and from the cannula assembly.

Pursuant to another feature of the present invention, the second laparoscopic instrument is inserted through the cannula assembly at an acute angle with respect to the first laparoscopic instrument.

According to a more specific feature of the present invention, the second laparoscopic instrument is inserted through a pair of side ports disposed on opposite sides of the cannula assembly and at locations staggered longitudinally or axially relative to one another.

According to another specific feature of the present invention, the cannula assembly includes a pair of tubular members connected to one another and disposed at an angle with respect to one another in the abdominal wall of the patient. Then, the step of forming the perforation includes the step of piercing the abdominal wall of the patient simultaneously with a pair of trocars connected to one another via the tubular members, the tubular members each taking the form of a trocar sleeve. Forming the perforation in the patient's abdominal wall also includes the step of piercing the abdominal wall of the patient simultaneously with a pair of trocars connected to one another via the tubular members, the tubular members each taking the form of a trocar sleeve. Where the tubular members are movably connected to one another, the method further comprises the step of moving the tubular members with respect to one another upon completion of the step of disposing.

In a specific implementation of the invention, moving the tubular members relative to one another includes the step of pivoting the tubular members with respect to one another about a point disposed essentially at the perforation.

According to another feature of the present invention, the second laparoscopic instrument is inserted through the cannula assembly essentially parallel to the first laparoscopic instrument. More specifically, the first laparoscopic instrument may be inserted through a first port at a proximal end of the cannula assembly and second laparoscopic instrument through a second port also at the proximal end of the cannula assembly, the second port being separate from the first port.

A laparoscopic cannula assembly and an associated laparoscopic method in accordance with the present invention facilitate laparoscopic surgery by enabling the temporary insertion of an extra instrument during a laparoscopic procedure. Pursuant to the method of the present invention, an extra laparoscopic instrument may be inserted into a patient's abdomen during laparoscopic surgery without requiring the formation of another perforation in the abdominal wall or the removal of a previously deployed instrument from the abdomen.

BRIEF DESCRIPTION OF THE DRAWING

FIG. 1 is a schematic perspective view, on a reduced scale, of a trocar sleeve or laparoscopic cannula, for use in a method in accordance with the present invention.

FIG. 2 is a schematic perspective view, on a reduced scale, of another trocar sleeve or laparoscopic cannula, for use in a method in accordance with the present invention.

FIG. 3 is a schematic perspective view, on a reduced scale, of a trocar sleeve or laparoscopic cannula, in accordance with the present invention.

FIG. 4 is a schematic perspective view, on a reduced scale, of a laparoscopic surgical method, in accordance with the present invention, using the trocar sleeve or laparoscopic cannula of FIG. 2.

DETAILED DESCRIPTION

Figure 5:
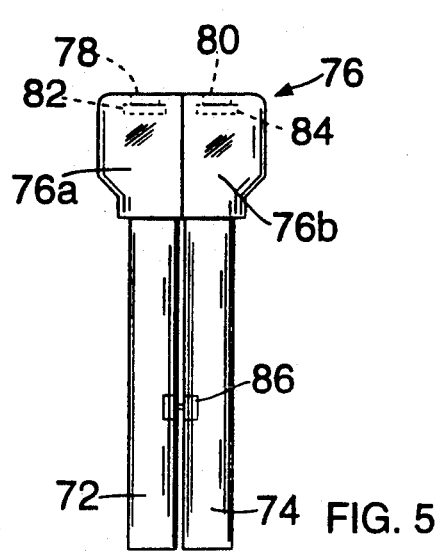
FIG. 5 is a schematic side elevational view of a laparoscopic cannula or trocar sleeve assembly in accordance with the present invention, showing the trocar sleeve assembly in an insertion configuration.

As illustrated in FIG. 1, a trocar sleeve or laparoscopic cannula 10 comprises a tubular member 12 having an exit opening 14 at a distal end and an insertion opening 16 at a proximal end for enabling the longitudinal passage through tubular member 12 of a first laparoscopic instrument (see FIG. 4). Tubular member 12 is further provided in a sidewall, distally of insertion opening 16, with an insertion aperture or port 18 on one side of tubular member 12. On a substantially opposite side of tubular member 12 is disposed an exit aperture or port 20 proximally of exit opening 14 and distally of insertion aperture 18. Apertures 18 and 20 define a linear passage or path 22 for a second laparoscopic instrument (see FIG. 4), the path being oriented at an acute angle with respect to tubular member 12. Trocar sleeve or laparoscopic cannula 10 is provided at its proximal end with a schematically represented conventional cap 24 which carries a one way valve or insufflation stopper (not illustrated).

As depicted in FIG. 2, another trocar sleeve or laparoscopic cannula 26 includes a body member in the form of a tube 28 having an exit opening 30 at a distal end and an insertion opening 32 at a proximal end for enabling the longitudinal passage through tube 28 of a first laparoscopic instrument 33 (FIG. 4). Tube 28 is further provided in a sidewall, distally of insertion opening 32, with an insertion aperture or port 34 on one side of tubular 28 member. Tube 28 is also provided in its sidewall with an exit aperture or port 36 on a substantially opposite side of tube 28, exit aperture 36 being located proximally of exit opening 30 and distally of insertion aperture 34. Apertures 34 and 36 define a linear passage or path 38 for a second laparoscopic instrument 39 (FIG. 4), the path being oriented at an acute angle a1 with respect to tube 28. Cannula 26 is provided at its proximal end with a schematically represented conventional cap 40 which carries a one way valve or insufflation stopper (not illustrated).

As further depicted in FIG. 2, cannula 26 includes a tubular arm 42 attached to tube 28 at insertion aperture 34. Arm 42 serves to guide auxiliary laparoscopic instrument 39 along passage or path 38. Accordingly, arm 42 is oriented along path 38 to facilitate insertion of auxiliary laparoscopic instrument 39 through exit aperture 36 upon insertion of laparoscopic instrument 39 through insertion aperture 34.

Cannula 26 is provided with an insufflation stopper 44 which is connected to tubular member 28 at insertion aperture 34.

FIG. 3 shows another trocar sleeve or laparoscopic cannula 46 provided at a proximal end with a cap 48 (schematically represented). End cap 48 includes a transversely oriented plate or wall 50 in which a pair of insertion openings or ports 52 and 54 are disposed. Each insertion port 52 and 54 is covered from the inside of cap 48 with a respect insufflation stopper or valve member 56 and 58 for inhibiting release of gaseous pressure through ports 52 and 54.

At an end opposite cap 48, cannula 46 has an exit opening 60. During a laparoscopic procedure, a primary laparoscopic instrument (not shown) may be inserted through port 52 along a substantially longitudinal path to exit opening 60. Subsequently, a second laparoscopic instrument (not shown) may be temporarily inserted through port 54 and exit opening 60. The operation of the two laparoscopic instruments simultaneously will be facilitated if the instruments have different shaft lengths. In that way, interference between the two instruments at the proximal end of trocar sleeve or laparoscopic cannula 46 will be minimized if not eliminated.

With cannula 46, the paths of the two laparoscopic instruments are approximately parallel to one another.

In performing a laparoscopic method utilizing a cannula 10, 26 or 46, a surgeon forms a perforation 62 (see FIG. 4) in an abdominal wall AW of a patient P. Upon the formation of perforation 62, a cannula as described hereinabove, for example, cannula 26, is disposed in the perforation so that cannula 26 traverses abdominal wall AW. A distal end of laparoscopic instrument 33, e.g., a grasping forceps, is inserted through tube 28 and into the patient's abdominal cavity (not designated). Subsequently, a distal end of auxiliary laparoscopic instrument 39 is inserted through tubular member 28 and into the patient's abdominal cavity while the first laparoscopic instrument 33 is partially disposed in cannula 26. More specifically, auxiliary instrument 39 is inserted through guide arm 42, tubular member 28 and exit aperture 36. Upon the insertion of auxiliary laparoscopic instrument 39, it is manipulated from outside the patient to perform a surgical operation inside the patient's abdomen. Subsequently, auxiliary laparoscopic instrument 39 is withdrawn from the patient's abdominal cavity and from the cannula 26.

During the afore-described procedure, another trocar sleeve or laparoscopic cannula 64 remains disposed in a respective perforation 66 in abdominal wall AW, an additional laparoscopic instrument 68 extending through cannula 64 into the patient's abdominal cavity. This third laparoscopic instrument 68 may take the form of a laparoscope or a video camera holder operatively connected to a monitor 70, another forceps, or another laparoscopic surgical instrument.

The auxiliary laparoscopic instrument 39 is most likely to take the form of an instrument which is needed only during a small portion of the entire laparoscopic procedure. Such an instrument might be, for example, a laser (shown in the drawing) or other cauterization instrument, an irrigator, a suction tube, an extra retractor, a clamp, a stapling or suturing device, or a clip applicator. The auxiliary laparoscopic instrument 39 operates on an internal body organ BO of patient P.

Naturally, trocar sleeve or laparoscopic cannula 10, 26, or 46 functions with relatively small-diameter instruments, as illustrated by the small sizes of instruments 33 and 39 (FIG. 4) relative to trocar tube 28. Of course, the diameter of a trocar sleeve or cannula in accordance with the present invention must be larger than the combined diameter of the two laparoscopic instruments inserted through the cannula in order to ensure passage of both laparoscopic instruments along their respective paths.

Figure 6:
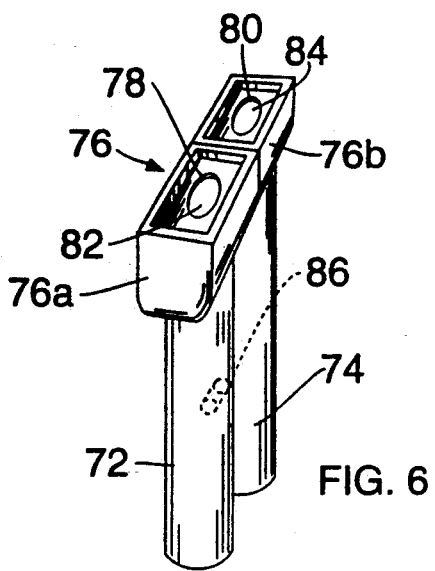
FIG. 6 is a schematic perspective view of the laparoscopic cannula or trocar sleeve assembly of FIG. 5.
Figure 7:
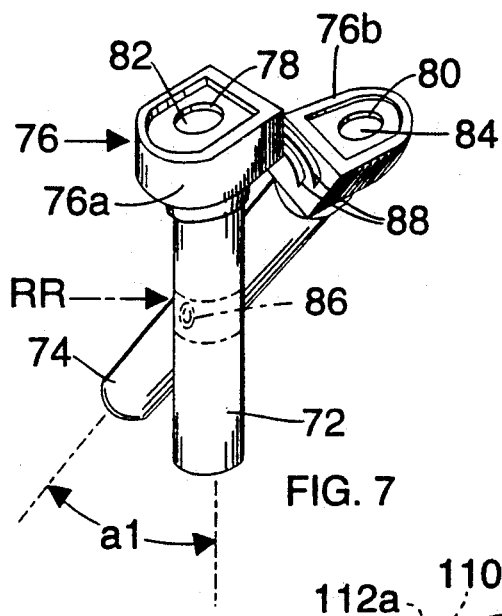
FIG. 7 is a schematic perspective view of the laparoscopic cannula or trocar sleeve assembly of FIGS. 5 and 6, showing the trocar sleeve assembly in an adjusted configuration.

As illustrated in FIGS. 5-7, a laparoscopic cannula or trocar sleeve assembly for use in laparoscopic surgery comprises a pair of rigid tubular members 72 and 74 connected to one another via an insufflation port 76 with a plurality of instrument insertion apertures 78 and 80 and associated insufflation stoppers 82 and 84 equal in number to the tubular members 72 and 74 and aligned therewith. Tubular members 72 and 74 may be rigid with port member 76 and, therefore, with one another. However, in the embodiment of FIGS. 5, 6, and 7, tubular members 72 and 74 are pivotably connected to one another at a central region by a pivot pin 86. In addition, port 76 includes a pair of port components 76a and 76b attached to the respective tubular members 72 and 74 and slidably connected to one another by a pair of arcuate rails 88 (FIG. 7), whereby tubular members 72 and 74 may be pivoted with respect to one another about pin 86, as illustrated in FIG. 7.

In using the laparoscopic cannula or trocar sleeve assembly of FIGS. 5-7, tubular members 72 and 74 are initially disposed in a parallel insertion configuration, illustrated in FIGS. 5 and 6. Each tubular member 72 and 74 and the associated port component 76a, 76b receives a respective trocar (not illustrated). The trocars are used to pierce the abdominal wall of a patient upon insufflation or pressurization of the abdominal cavity via a Veress needle. Upon piercing of the abdominal wall and removal of the trocars, tubular members 72 and 74 may be pivoted relative to one another to form the configuration of FIG. 7 wherein an desired angle a1 is formed between tubular members 72 and 74. Laparoscopic instruments may be inserted through apertures 78 and 80 and tubular member 72 and 74 so that the distal ends of the instruments are positioned in a patient's abdominal cavity and can be manipulated from outside the patient to perform surgical operations on the patient's internal organs.

Tubular member 72 and its respective port component 76a and instrument insertion aperture 78 define, for a first laparoscopic instrument having a rigid shaft, a first insertion path through a pre-established instrument-crossing region RR of predetermined area to be lodged in a patient's abdominal wall. Region RR is preferably an area about pin 86, where the distance between tubular members 72 and 74 remains essentially constant even though the tubular members 72 and 74 are pivoted with respect to one another during an operation. Region RR is the place where two laparoscopic instruments cross one another in an angled configuration of the laparoscopic cannula or trocar sleeve assembly (FIG. 7) and has a predetermined area slightly greater than the combined transverse cross-sectional areas of tubular members 72 and 74.

Tubular member 74, together with its respective port component 76b and instrument insertion aperture 80, defines, for a second laparoscopic instrument having a rigid shaft, a respective insertion path through instrument-crossing region RR.

Figure 8:
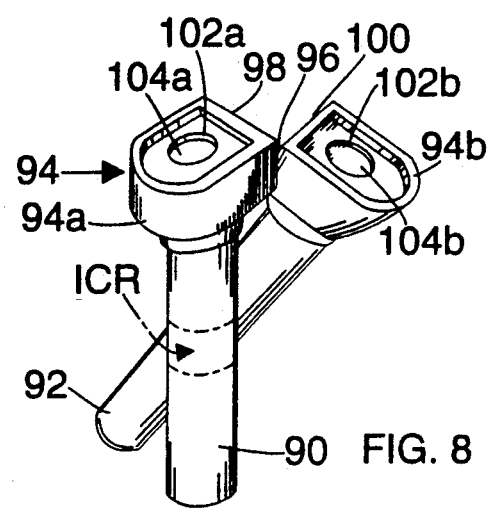
FIG. 8 is a schematic perspective view of another laparoscopic cannula or trocar sleeve assembly, showing the assembly in an adjusted configuration.

As illustrated in FIG. 8, another laparoscopic cannula or trocar sleeve assembly for use in laparoscopic surgery comprises a pair of rigid tubular members 90 and 92 connected to one another via an insufflation port subassembly 94. Port subassembly 94 comprises a pair of port components 94a and 94b attached to the proximal ends of the respective tubular members 90 and 92. Port components 94a and 94b are pivotably connected to one another along an edge 96 which is inclined with respect to tubular members 90 and 92. Accordingly, tubular members 90 and 92 can be pivoted from an insertion configuration to an angled configuration (FIG. 8) and back again. In the insertion configuration (compare FIG. 5), tubular members 90 and 92 are parallel to one another and edges 98 and 100 of port components 94a and 94b are contiguous and parallel.

Port components 94a and 94b have respective instrument insertion apertures 102a and 102b coverable by respective spring loaded insufflation stoppers 104a and 104b.

In using the laparoscopic cannula or trocar sleeve assembly of FIG. 8, tubular members 90 and 92 are initially disposed in a parallel insertion configuration. Each tubular member 90 and 92 and the associated port component 94a and 94b receives a respective trocar (not illustrated) for piercing the abdominal wall of a patient upon insufflation or pressurization of the abdominal cavity. Upon piercing of the abdominal wall and removal of the trocars, tubular members 90 and 92 may be pivoted relative to one another to form the configuration of FIG. 8 wherein an desired angle is formed between tubular members 90 and 92.

Tubular member 90 and its respective port component 94a and instrument insertion aperture 102a define, for a first laparoscopic instrument having a rigid shaft, a first insertion path through a pre-established instrument-crossing region ICR of predetermined area to be lodged in a patient's abdominal wall. Region ICR is preferably an area where the distance between tubular members 90 and 92 remains essentially constant even though the tubular members 90 and 92 are pivoted with respect to one another during an operation. Region ICR is the place where two laparoscopic instruments cross one another in an angled configuration of the laparoscopic cannula or trocar sleeve assembly (FIG. 8) and has a predetermined area slightly greater than the combined transverse cross-sectional areas of tubular members 90 and 92.

Tubular member 92, together with its respective port component 94b and instrument insertion aperture 102b, defines, for a second laparoscopic instrument having a rigid shaft, a respective insertion path through instrument-crossing region ICR.

Figure 9:
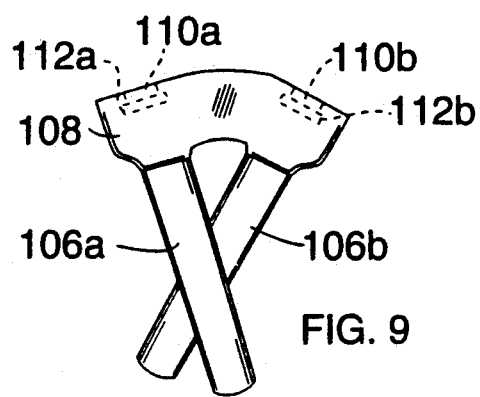
FIG. 9 is a schematic side elevational view of a further laparoscopic cannula or trocar sleeve assembly in accordance with the present invention.

As shown in FIG. 9, a laparoscopic cannula or trocar sleeve assembly for use in laparoscopic surgery comprises a pair of rigid tubular members 106a and 106b each rigidly connected to an integral insufflation port member 108 having two insertion ports or apertures 110a and 110b and associated spring loaded insufflation stoppers 112a and 112b.

In using the laparoscopic cannula or trocar sleeve assembly of FIG. 9, tubular members 106a and 106b are traversed by respective trocars (not illustrated) for piercing the abdominal wall of a patient upon insufflation or pressurization of the abdominal cavity. Upon piercing of the abdominal wall, the laparoscopic cannula or trocar sleeve assembly is positioned so that a pre-established instrument-crossing region TB of predetermined area is lodged in the patient's abdominal wall. Region TB is the area where the distance between tubular members 106a and 106b is a minimum. Region TB is the place where two laparoscopic instruments cross one another in an angled configuration of the laparoscopic cannula or trocar sleeve assembly and has a predetermined area slightly greater than the combined transverse cross-sectional areas of tubular members 106a and 106b.

Tubular members 106a and 106b define respective laparoscopic instrument insertion paths.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A cannula assembly for use in laparoscopic surgery, comprising:
   a rigid tubular member;
   first means connected to said tubular member and rigid therewith for defining, for a first laparoscopic instrument having a rigid shaft, a first insertion path through said tubular member and through a region of predetermined area to be lodged in a patient's abdomen;
   second means connected to said tubular member and at least partially separate from said first means for defining, for a second laparoscopic instrument having a rigid shaft, a second insertion path through said region; and
   angle means on said tubular member for angling said first insertion path and said second insertion path relative to one another so that said first laparoscopic instrument and said second laparoscopic instrument emerge from a distal end of the cannula assembly at an angle relative to one another.

2. The assembly defined in claim 1 wherein said first means includes a port component attached to said tubular member at one end thereof, said second means including a rigid tube attached to said tubular member.

3. The assembly defined in claim 2 wherein angle means includes attachment means for pivotably attaching said tube to said tubular member about said region.

4. The assembly defined in claim 2 wherein said angle means includes attachment means for rigidly attaching said tube to said tubular member.

5. The assembly defined in claim 2 wherein said tube is attached to said tubular member via said port component, said port component also serving as a proximal port for said tube, said port component being part of said angle means.

6. The assembly defined in claim 2 wherein said tube is provided at one end with a port attachment, said angle means including connection means for movably connecting said port attachment to said port component.

7. The assembly defined in claim 3 wherein said connection means includes means for slidably connecting said port attachment to said port component.

8. The assembly defined in claim 3 wherein said connection means includes means for pivotably connecting said port attachment to said port component.

9. A cannula assembly for use in laparoscopic surgery, comprising:
a rigid first tubular member having a first proximal end, a first distal end and a first central region;
a rigid second tubular member having a second proximal end, a second distal end and a second central region; and
connection means on said first tubular member and said second tubular member for connecting said first tubular member and said second tubular member to one another at said first proximal end and said second proximal end, said connection means including angle means for enabling a distal end of a first laparoscopic instrument inserted through said first tubular member to be disposed at an angle with respect to a distal end of a second laparoscopic instrument inserted through said second tubular member.

10. The assembly defined in claim 9 wherein said first tubular member is oriented permanently at an angle with respect to said second tubular member.

11. The assembly defined in claim 9 wherein said first tubular member is connected to said second tubular member essentially only at said second proximal region and said second central region, said second tubular member being connected to said first tubular member only at said first proximal end and said first central region.

12. The assembly defined in claim 11 wherein said angle means includes means for movably connecting said first central region to said second central region and for movabling connecting said first proximal end to said second proximal end.

13. The assembly defined in claim 12 wherein said angle means includes means for pivotably connecting said first central region to said second central region and for slidably connecting said first proximal end to said second proximal end.

14. The assembly defined in claim 9 wherein said first tubular member is connected to said second tubular member essentially only at said second proximal region, said second tubular member being connected to said first tubular member only at said first proximal end.

15. A method for use in laparoscopy, comprising the steps of:
forming a perforation in a patient's abdominal wall;
disposing in said perforation a cannula assembly including at least one rigid tubular member;
inserting a distal end of a first laparoscopic instrument through said cannula assembly and into the patient's abdominal cavity;
inserting a distal end of a second laparoscopic instrument through said cannula assembly and into the patient's abdominal cavity so that the distal ends of said first laparoscopic instrument and said second laparoscopic instrument extend at an acute angle relative to one another inside the patient's abdominal cavity;
manipulating said second laparoscopic instrument from outside the patient to perform a surgical operation inside the patient; and
withdrawing said second laparoscopic instrument from the patient's abdominal cavity and from said cannula assembly.

16. The method defined in claim 15 wherein said cannula assembly includes a pair of tubular members connected to one another and disposed at an angle with respect to one another in the abdominal wall of the patient.

17. The method defined in claim 15 wherein said second laparoscopic instrument is inserted through said cannula assembly essentially parallel to said first laparoscopic instrument.

18. The method defined in claim 17 wherein said first laparoscopic instrument is inserted through a first port at a proximal end of said cannula assembly and wherein second laparoscopic instrument is inserted through a second port also at said proximal end of said cannula assembly, said second port being separate from said first port.

19. The method defined in claim 15 wherein said second laparoscopic instrument is inserted through a pair of side ports disposed on opposite sides of said cannula assembly and at locations staggered longitudinally or axially relative to one another.

20. The method defined in claim 19 wherein said tubular members are rigidly connected to one another, said step of forming said perforation including the step of piercing the abdominal wall of the patient simultaneously with a pair of trocars connected to one another via said tubular members, said tubular members each taking the form of a trocar sleeve.

21. The method defined in claim 19 wherein said tubular members are movably connected to one another, said step of forming said perforation including the step of piercing the abdominal wall of the patient simultaneously with a pair of trocars connected to one another via said tubular members, said tubular members each taking the form of a trocar sleeve, further comprising the step of moving said tubular members with respect to one another upon completion of said step of disposing.

22. The method defined in claim 21 wherein said step of moving includes the step of pivoting said tubular members with respect to one another about a point disposed essentially at said perforation.

* * * * *